Nov. 28, 1933. W. F. YERKES Plant Pat. 84
PEACH
Filed Oct. 28, 1932
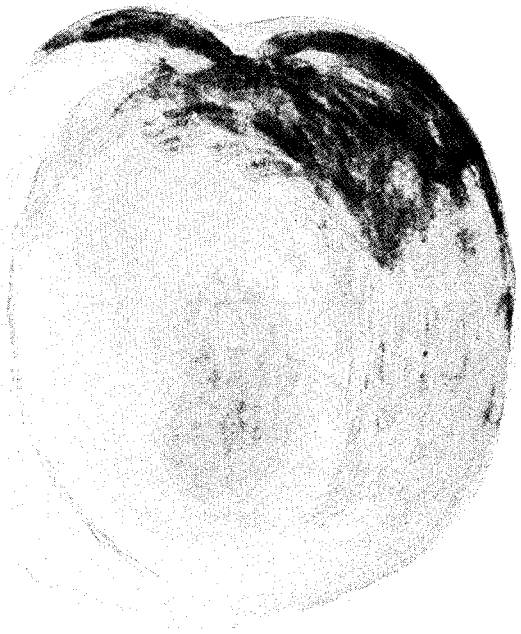
INVENTOR
*Wm F. Yerkes*
BY Percy S. Wilson
ATTORNEY

UNITED STATES PATENT OFFICE

84

PEACH

William F. Yerkes, near Rio Oso, Calif.

Application October 28, 1932. Serial No. 640,063

1 Claim. (Cl. 47—62)

My discovery relates to improvements in peach rees and the fruit of the same.

*Origin.*—My improved peach originated as a hance seedling which I discovered on my ranch ıear Rio Oso, Sutter County, California, and which was raised by me to maturity and recognized to be of a distinctive variety having novel characteristics from other varieties and being particularly characterized by its period of ripening.

From the parent seedling I have asexually reproduced a number of other trees through the medium of June budding, which additional trees so propagated have held true to the characteristics of the parent seedling as to period of ripening and quality and character of the fruit produced, and proven the permanency thereof.

It is probable that the parent seedling was produced from a Late Crawford pollenized with a Tuscan Cling. My improved peach has, in its large size, yellow flesh, fine grain, firm texture, an excellent peach flavor, and a slight ridge of the surface, some of the characteristics of the Late Crawford; while in the surface color, red at the pit, and slightly spicy flavor, it has the characteristics of a Tuscan Cling.

The set of the fruit each year has been extremely heavy and has required extremely radical thinning—nine out of ten peaches being pulled off to one that was allowed to remain, and under this radical thinning the trees have each year borne all the trees could carry, evidence that my new peach is self pollenizing.

*Tree.*—Tree is a very vigorous and upright grower. Wood appears to be of well toughened fiber; limbs are not easily broken and carry their load of fruit well. Bark on old wood is comparatively smooth and of a grey-reddish hue. Branches and twigs are stocky. Tree bears young, and is regularly productive, requiring annual thinning.

*Foliage.*—The leaves are approximately 1½ inches wide, and 5 to 6 inches long; base acute; apex pointed; margin inclined to be wavy with shallow scallops, and with minute reddish barbs or tips. The upper surface of the foliage is glossy and of a gun-metal green. The lower surface is smooth and apple-green. There are usually two reniform glands on a leaf stem, and usually also one or two on the base of the leaf.

*Bloom.*—Bloom is extremely large; petals are large and spread out flat. Petals are a light rose pink, almost white, with a dark pink center. The bloom is very showy. My new peach in bloom gives almost the same effect as a pinkish white ornamental flowering peach.

*Seed.*—Seed is comparatively small in proportion to size of fruit, averaging in size from ⅞ to 1 inch wide, ⅝ to ¾ inch thick, and 1¼ to 1½ inches long. Form of seed is an elongated oval and pointed; convolutions normal.

*Fruit.*—The new peach is a perfect freestone; is of extreme large size, averaging in diameter from 2¾ to 3¾ inches measured from end to end. Form is globular, slightly elongated, with a slight low ridge along the line of suture.

The surface of the fruit is moderately covered with short greyish fuzz, readily removable.

The ground color of the peach is a rich orange yellow. Beginning at the stem of the peach on one side the ground color is overspread with a very dark, almost black crimson, running out to a lighter crimson and into a rich mottle of crimson over the orange yellow. The black crimson covers from fifteen to twenty-five per cent of the surface, the lighter crimson and mottle covering from fifteen to twenty-five per cent leaving, according to variations of individual peaches, from thirty-three and one third per cent to fifty per cent of the orange yellow.

Flesh is a deep yellow, very fine grained, and of firm texture.

Flavor is very excellent, rich, juicy and sweet—slightly spicy.

*Maturity.*—My new peach matures during the intermission of four weeks between the going out of such varieties as J. H. Hale, Lovell, Elberta and similar varieties of peach and the ripening of Salwey, during which intermission there has not heretofore been any good yellow freestone peach available. It matures about two weeks after the J. H. Hale peach.

My new peach when mature hangs well on the tree, and shows very little tendency to windfall.

It is to be understood that the foregoing characteristics are typical but subject, perhaps, to slight variations which may arise by reason of change of environment.

I claim:

The peach tree herein described characterized by the ripening period of its fruit relative to the period of ripening of similar varieties; the heavy set of the fruit on the tree; and the globular, slightly elongated shape of said fruit with a moderate ridge along the line of suture.

WILLIAM F. YERKES.